United States Patent [19]
Kyle et al.

[11] 3,952,158
[45] Apr. 20, 1976

[54] EAR PROTECTION AND HEARING DEVICE

[76] Inventors: Gordon L. Kyle, 1607 12th St., Decatur, Ala. 35601; John D. Hays, Jr., Rte. 1, Box 175, Owens Cross Roads, Ala. 35763

[22] Filed: Aug. 26, 1974

[21] Appl. No.: 500,734

[52] U.S. Cl.............................. 179/1 P; 179/156 R
[51] Int. Cl.² ......................................... H04M 1/19
[58] Field of Search............. 179/1 P, 107 R, 156 R, 179/1 D

[56] References Cited
UNITED STATES PATENTS

| | | | |
|---|---|---|---|
| 3,306,991 | 2/1967 | Wood............................ | 179/107 R |
| 3,394,226 | 7/1968 | Andrews........................... | 179/1 D |

Primary Examiner—William C. Cooper

[57] ABSTRACT

A device for protecting the ears from loud sounds while enabling low-level voice frequency sounds to be discerned. A microphone is positioned on the outside of an insulated ear protector and a sound reproducer positioned within the protector. The sound picked up by the microphone is subjected to audio amplitude compression and voice frequency bandpass filtering before being converted back to sound.

3 Claims, 5 Drawing Figures

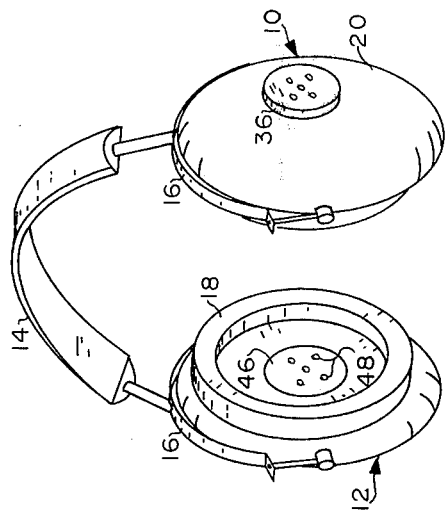
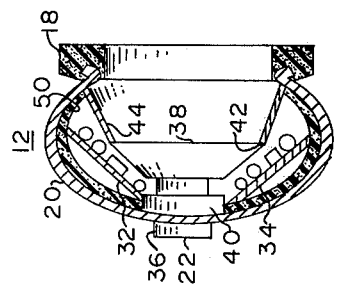
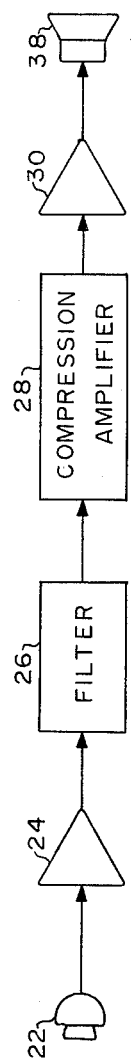
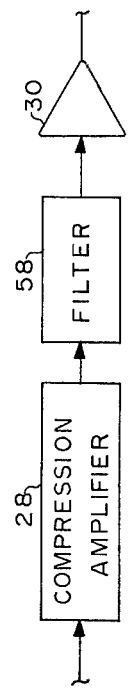
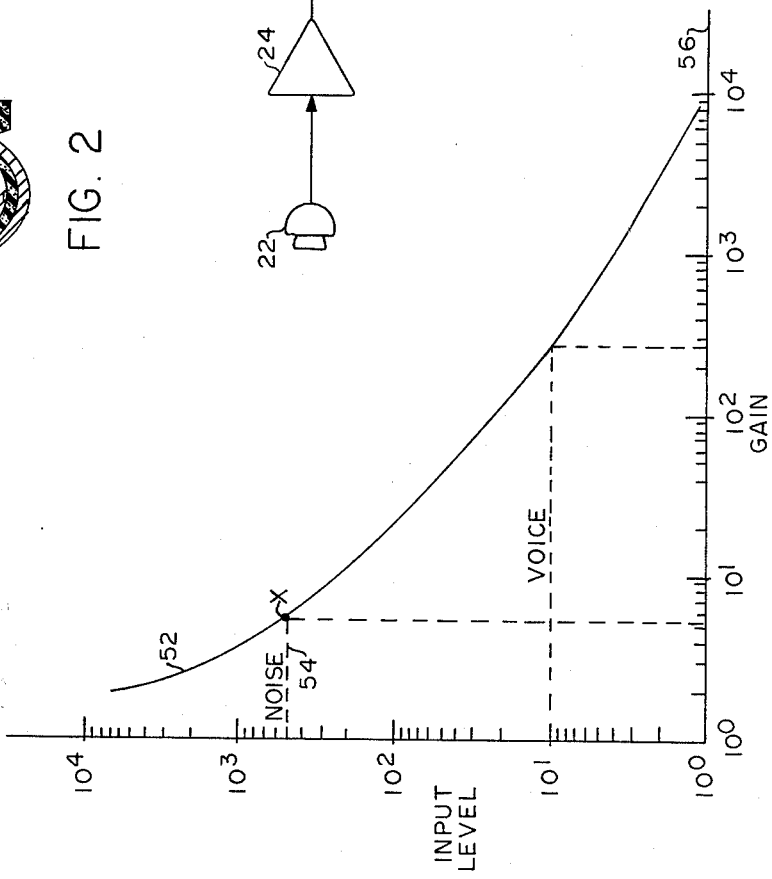

EAR PROTECTION AND HEARING DEVICE

BACKGROUND OF THE INVENTION

1. Field of the Invention

This invention relates to ear protection devices, and particularly to such a device wherein means are provided for enabling the wearer to hear low-level voice sounds despite the presence of high-level noise signals.

2. General Description of the Prior Art

Noise pollution is clearly a growing problem. It has, however, been with us sufficiently long enough for the subject to have been given substantial consideration and some corrective measures and protection devices developed. For example, sound-insulating earmuffs are now available, and these are worn in certain noise areas, particularly at airports near jet aircraft and in some manufacturing installations. The difficulty with such devices is, however, that desired or necessary communications between persons wearing them are often impossible or exceedingly difficult.

SUMMARY OF THE INVENTION

In accordance with this invention, an earmuff-type enclosure is fitted with a sound reproducer or earphone. In addition, a microphone is placed on the outside of the device, and its output is supplied through a bandpass filter, amplifier, and compression device to the sound reproducer. In this fashion, high amplitude noise frequencies are attenuated with respect to low amplitude voice frequencies, and thus the wearer of the device can hear voice communications of much less intensity than typical noise sounds. The invention is aided by the fact that noise frequencies typically have a relatively fixed content of frequencies wherein communication frequencies, e.g., voice frequencies, vary in frequency and level to a more considerable extent, whereby the system of the present invention effects a desired discrimination between noise and communication frequencies.

The wearer of the device can also perceive direction of sounds by virtue of the fact that each earmuff contains identical circuits such that when adjusted for the same sound level output, they allow the ears to discriminate between amplitude and phase.

BRIEF DESCRIPTION OF THE DRAWINGS

FIG. 1 is a pictoral view of an embodiment of the invention.

FIG. 2 is a sectional view as it would be seen by cutting a vertical plane through one of the ear protectors shown in FIG. 1, the cut being normal to the front and back sides of a protector.

FIG. 3 is a block diagram of the electrical components of the device.

FIG. 4 is a graph of the typical response of a compression amplifier suitable for employment by the invention.

FIG. 5 is an electrical block diagram illustrative of a modification to the one shown in FIG. 3.

DETAILED DESCRIPTION OF THE DRAWINGS

Referring to the drawings, there is shown in FIG. 1 an embodiment of the invention which includes a pair of identical ear protectors 10 and 12 interconnected by headband 14. Each protector is connected to headband 14 by circular yoke 16 so that protectors 10 and 12 are seated against each ear and sealed from external noises by a soft, pliable ear cushion 18. Each ear protector also includes an ovular-shaped housing or shell 20 (FIG. 2) within which are mounted the various electrical components of the ear protection system of this invention.

As shown in FIG. 3, the system for each protector includes microphone 22, linear amplifier 24, filter 26, compression amplifier 28, and power amplifier 30, which are interconnected in this serial order. Except for microphone 22, these components are assembled on a pair of printed circuit cards 32 and 34, which are supported within the ear protector. Microphone 22 is supported within receptacle 36 (FIGS. 1 and 2) centrally formed on the outer ovate surface of ear protector 12, shown in FIG. 2. Speaker 38 is connected as an output of power amplifier 30 and is supported by sound-insulating cushion 40 and by inner rim 42 of conical speaker baffle 44. Audio from the speaker passes through speaker grille 46 (FIG. 1), which is provided with a plurality of openings 48. Sound-absorbing lining, or insulation 50 is disposed about the inner surface of protector 12 so as to prevent feedback between speaker 38 and microphone 22, and, of course, to prevent ambient noise from being conducted into the protectors directly through housing 20.

Sounds from the environment are detected by microphone 22 and are subject to the response of the microphone (typically 30 to 16,000 Hz). All frequencies of the received audio spectrum are fed to amplifier 24. Amplifier 24 amplifies the weak microphone signals to a voltage level suitable for processing by active filter 26. Filter 26 is basically a bandpass filter which may include various combinations of low-pass, bandpass, high-pass and notch filters in order to decrease or exclude frequencies which are lower in frequency or higher in frequency than the desired audio band selected for conveying intelligible speech to the wearer of the protector. Typically, the bandpass would be that necessary for intelligible speech.

At this point, it is to be observed that in any noise-polluted environment it is to be expected that unwanted noise will be of a much higher level than a normal speaking voice and will have different combinations of recurring frequencies at different power levels than a speaking voice. Accordingly, the present invention, by means of compression amplifier 28 and selected filtering, reduces the level of noise frequencies to essentially a below par status with respect to voice frequencies, allowing the latter to become dominant and to be clearly audible. Under the same conditions without the applicants' device, it has been found that the voice frequencies are not discernable to the ear over the noise frequencies. One further factor contributing to this result would appear to be that by limiting the intensity of a noise signal which can be supplied the ear, the ear does not become saturated or disabled by loud noise signals and thus remains sensitive to lower-level voice sounds. Conversely, as will be appreciated, when the ear is directly exposed to a loud sound, there is a finite period for recovery after the loud sound had dissipated, during which period the ear is not responsive to lower-level sounds.

FIG. 4 shows normalized output curve 52 of compression amplifier 28. This curve is obtained by plotting the input of compression amplifier 28 in relation to the gain of compression amplifier 28. As an example of operation of compression amplifier 28, it is assumed that a voice signal and a noise signal are passed simultaneously through filter 26 to the input of compression amplifier 28. It is further assumed that the amplitude of the voice signal is 10 units and the amplitude of the noise signal is 500 units at the input of compression amplifier 28.

As shown in FIG. 4, a reference line 54 drawn parallel to base line 56 shows that the 500 unit signal level of the noise input intersects gain curve 52 at point X, and the vertical line drawn to base line 56 shows that the gain of compression amplifier 28 at this level of input would be 5.5. Accordingly, the output amplitude would be the signal input 500 times 5.5, which would produce an output level of 2,750 units. Since the voice amplitude input is 10 units, the gain on the amplifier is shown to be 280. Thus, a voice output would be at a level of 2,800 units. It is readily deduced from the above that compression amplifier 28 can be tailored to fit various noise situations.

The output of compression amplifier 28 is connected as an input to power amplifier 30, which boosts the output of compression amplifier 28 to a level suitable for driving speaker 38 to a reasonable listening level within ear protectors 10 and 12.

FIG. 5 illustrates that an additional bandpass filter 58 may be desirable in the general circuit shown in FIG. 3, it being inserted between compression amplifier 28 and power amplifier 30. By its inclusion, additional frequency discrimination is accomplished, which serves to decrease the amplitude of frequencies at the output of compression amplifier 28 falling outside the bandpass of the filters. The frequencies eliminated are those which have been insufficiently reduced by filter 26 and frequencies resulting from distortion products generated within compression amplifier 28.

From the foregoing, it will be appreciated that the applicants have provided an improved ear protector, a protector which not only protects the ear against loud noises but allows a wearer to hear and understand communications within a selected frequency band.

What is claimed is:

1. An ear protection and hearing device comprising:

at least one enclosure having an open region adapted to fit around the human ear;
   a sound insulating layer providing a barrier surface between the inside and outside of said enclosure;
   a microphone attached to and positioned on the outside of said enclosure;
   filter means having an input and output and including means for passing a selected band of audible frequencies;
   compression means having an amplitude transfer factor which varies inversely with input;
   signal amplification means;
   a sound reproducer within said enclosure; and
   means for serially connecting said filter means, said compression means, and said amplification means, electrically, in this order, between said microphone and said sound reproducer;
   whereby a selected range of low level sounds are discernable in the presence of higher level noise.

2. A device as set forth in claim 1 further comprising a second filter means for passing a selected band of audible frequencies, corresponding to that passed by said first-named filter means, said second filter means being serially positioned between said microphone and said speaker and subsequent to said compression means.

3. A device as set forth in claim 1 further comprising a second like enclosure, a second like sound insulating layer, a second like microphone, a second like filter means, second like compression means, second like sound amplification means, second like sound reproduction means, and second like means for serially connecting said filter means, said compression means, and said amplification means electrically, in that order, between said second microphone and said second sound reproducer, and still further comprising flexible support means adapted to be worn over the head, and including means for positioning said enclosures in a spaced relation over the ears of a wearer.

* * * * *